(12) United States Patent
Jaffe et al.

(10) Patent No.: US 8,309,940 B2
(45) Date of Patent: Nov. 13, 2012

(54) LIGHTING DESIGN OF HIGH QUALITY BIOMEDICAL DEVICES

(75) Inventors: Claudia B. Jaffe, Portland, OR (US); Steven M. Jaffe, Portland, OR (US); Arlie R. Conner, Portland, OR (US)

(73) Assignee: Lumencor, Inc., Beaverton, OR (US)

( * ) Notice: Subject to any disclaimer, the term of this patent is extended or adjusted under 35 U.S.C. 154(b) by 0 days.

(21) Appl. No.: 13/484,031

(22) Filed: May 30, 2012

(65) Prior Publication Data
US 2012/0236585 A1 Sep. 20, 2012

Related U.S. Application Data

(63) Continuation of application No. 13/416,125, filed on Mar. 9, 2012, which is a continuation of application No. 12/691,601, filed on Jan. 21, 2010.

(60) Provisional application No. 61/147,040, filed on Jan. 23, 2009.

(51) Int. Cl.
*G01J 1/58* (2006.01)
(52) U.S. Cl. .................................... 250/459.1
(58) Field of Classification Search ................. 250/459.1
See application file for complete search history.

(56) References Cited

U.S. PATENT DOCUMENTS

| | | |
|---|---|---|
| 1,998,054 A | 4/1935 | McBurney |
| 3,313,337 A | 4/1967 | Bernat |
| 3,637,285 A | 1/1972 | Stewart |
| 3,759,604 A | 9/1973 | Thelen |
| 3,881,800 A | 5/1975 | Friesem |
| 3,982,151 A | 9/1976 | Ludovici |
| 4,003,080 A | 1/1977 | Maiman |
| 4,298,820 A | 11/1981 | Bongers |
| 4,371,897 A | 2/1983 | Kramer |
| 4,510,555 A | 4/1985 | Mori |
| 4,539,687 A | 9/1985 | Gordon |
| 4,602,281 A | 7/1986 | Nagasaki et al. |
| 4,626,068 A | 12/1986 | Caldwell |
| 4,642,695 A | 2/1987 | Iwasaki |
| 4,644,141 A | 2/1987 | Hagen |
| 4,657,013 A | 4/1987 | Hoerenz et al. |
| 4,695,332 A | 9/1987 | Gordon |
| 4,695,732 A | 9/1987 | Ward |
| 4,695,762 A | 9/1987 | Berkstresser |
| 4,713,577 A | 12/1987 | Gualtieri |
| 4,724,356 A | 2/1988 | Daehler |
| 4,798,994 A | 1/1989 | Rijpers |

(Continued)

FOREIGN PATENT DOCUMENTS
CA 2 280 398 4/2000
(Continued)

OTHER PUBLICATIONS

International Search Report dated Dec. 31, 2008, Application No. PCT/US2008/072394, 10 pages.

(Continued)

*Primary Examiner* — David Porta
*Assistant Examiner* — Hugh H Maupin
(74) *Attorney, Agent, or Firm* — Fliesler Meyer LLP (57) ABSTRACT

The invention relates to a plurality of light sources to power a variety of applications including microarray readers, microplate scanners, microfluidic analyzers, sensors, sequencers, Q-PCR and a host of other bioanalytical tools that drive today's commercial, academic and clinical biotech labs.

28 Claims, 3 Drawing Sheets

U.S. PATENT DOCUMENTS

| | | |
|---|---|---|
| 4,804,850 A | 2/1989 | Norrish et al. |
| 4,852,985 A | 8/1989 | Fujihara et al. |
| 4,937,661 A | 6/1990 | Van Der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza et al. |
| 5,803,579 A | 9/1998 | Turnbull et al. |
| 5,804,919 A | 9/1998 | Jacobsen |
| 5,808,759 A | 9/1998 | Okamori et al. |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu |
| 6,614,161 B1 | 9/2003 | Jacobsen et al. |
| 6,614,179 B1 | 9/2003 | Shimizu et al. |
| 6,637,905 B1 | 10/2003 | Ng |
| 6,642,652 B2 | 11/2003 | Collins et al. |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler et al. |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rain, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |
| 7,083,610 B1 | 8/2006 | Murray et al. |
| 7,141,801 B2 | 11/2006 | Goodwin |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 | 1/2008 | Rutherford et al. |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |
| 7,467,885 B2 | 12/2008 | Grotsch et al. |
| 7,488,088 B2 | 2/2009 | Brukilacchio |
| 7,488,101 B2 | 2/2009 | Brukilacchio |
| 7,498,734 B2 | 3/2009 | Suehiro et al. |
| 7,540,616 B2 | 6/2009 | Conner |
| 7,633,093 B2 | 12/2009 | Blonder et al. |
| 7,709,811 B2 | 5/2010 | Conner |
| 7,746,560 B2 | 6/2010 | Yamazaki |
| 7,832,878 B2 | 11/2010 | Brukilacchio |
| 7,837,348 B2 | 11/2010 | Narendran et al. |
| 7,854,514 B2 | 12/2010 | Conner |
| 7,857,457 B2 | 12/2010 | Rutherford et al. |
| 8,029,142 B2 | 10/2011 | Conner |
| 8,098,375 B2 * | 1/2012 | Brukilacchio ............ 356/432 |
| 2001/0055208 A1 | 12/2001 | Kimura |
| 2002/0109844 A1 | 8/2002 | Christel et al. |
| 2002/0127224 A1 | 9/2002 | Chen |
| 2003/0044160 A1 | 3/2003 | Jonese et al. |
| 2003/0095401 A1 | 5/2003 | Hanson et al. |
| 2003/0127609 A1 | 7/2003 | El-Hage et al. |
| 2003/0160151 A1 | 8/2003 | Zarate et al. |
| 2003/0230728 A1 | 12/2003 | Dai |
| 2003/0233138 A1 | 12/2003 | Spooner |
| 2004/0090600 A1 | 5/2004 | Blei |
| 2004/0247861 A1 | 12/2004 | Naasani |
| 2005/0062404 A1 | 3/2005 | Jones et al. |
| 2005/0116635 A1 | 6/2005 | Walson et al. |
| 2005/0146652 A1 | 7/2005 | Yokoyama et al. |
| 2005/0152029 A1 | 7/2005 | Endo |
| 2005/0184651 A1 | 8/2005 | Cheng |
| 2005/0201899 A1 | 9/2005 | Weisbuch |
| 2005/0248839 A1 | 11/2005 | Yamaguchi |
| 2005/0260676 A1 | 11/2005 | Chandler |
| 2005/0263679 A1 | 12/2005 | Fan |
| 2006/0002131 A1 | 1/2006 | Schultz et al. |
| 2006/0030026 A1 | 2/2006 | Garcia |
| 2006/0060872 A1 | 3/2006 | Edmond et al. |
| 2006/0060879 A1 | 3/2006 | Edmond |
| 2006/0114960 A1 | 6/2006 | Snee |
| 2006/0170931 A1 | 8/2006 | Guo |

| | | | |
|---|---|---|---|
| 2006/0237658 | A1 | 10/2006 | Waluszko |
| 2006/0282137 | A1 | 12/2006 | Nightingale et al. |
| 2007/0053184 | A1 | 3/2007 | Brukilacchio |
| 2007/0053200 | A1 | 3/2007 | Brukilacchio |
| 2007/0058389 | A1 | 3/2007 | Brukilacchio |
| 2007/0064202 | A1 | 3/2007 | Moffat et al. |
| 2007/0086006 | A1 | 4/2007 | Ebersole et al. |
| 2007/0126017 | A1 | 6/2007 | Krames et al. |
| 2007/0211460 | A1 | 9/2007 | Ravkin |
| 2007/0253733 | A1 | 11/2007 | Fey |
| 2007/0279914 | A1 | 12/2007 | Rutherford et al. |
| 2007/0279915 | A1 | 12/2007 | Rutherford et al. |
| 2007/0280622 | A1 | 12/2007 | Rutherford et al. |
| 2007/0281322 | A1 | 12/2007 | Jaffe et al. |
| 2007/0284513 | A1 | 12/2007 | Fan |
| 2007/0297049 | A1 | 12/2007 | Schadwinkel et al. |
| 2008/0079910 | A1 | 4/2008 | Rutherford et al. |
| 2008/0224024 | A1 | 9/2008 | Ashdown |
| 2008/0291446 | A1 | 11/2008 | Smith |
| 2009/0122533 | A1 | 5/2009 | Brukilacchio |
| 2009/0196046 | A1 | 8/2009 | Rutherford et al. |
| 2009/0268461 | A1 | 10/2009 | Deak et al. |
| 2010/0188017 | A1 | 7/2010 | Brukilacchio |

FOREIGN PATENT DOCUMENTS

| | | |
|---|---|---|
| EP | 1 426 807 | 12/2003 |
| GB | 0943756 | 12/1963 |
| GB | 2 000 173 A | 1/1979 |
| JP | 02-804873 | 7/1998 |
| JP | 2005-195485 | 7/2005 |
| JP | 2005-243973 | 9/2005 |
| JP | 2006-049814 | 2/2006 |
| JP | 2007-133435 | 5/2007 |
| KR | 10-2006-0055934 | 5/2006 |
| KR | 10-2006-0089104 | 8/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report for PCT/US2010021843 dated Aug. 19, 2010, 9 pages.
Extended European Search Report for PCT/US2008072394 dated Oct. 7, 2011, 9 pages.
International Search Report dated Jun. 19, 2012 for Application No. PCT/US2011/063030.
Lauer, Herbert F., "Exposure Meter for Precision Light Dosage", The Review of Scientific Instruments, vol. 20, No. 2, Feb. 1949, pp. 103-109.
Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).
Vlasenko, N.A., et al., "Interference of Luminescent Emission from an Evaporated Phosphor," Opt. Spect., vol. 11, pp. 216-219 (1961).
Vlasenko, N.A., et al., "Investigation of Interference Effects in Thin Electroluminescent ZnS-Mn Films," Opt. Spect., vol. 28, pp. 68-71 (1970).
Poelman, D., et al., "Spectral Shifts in Thin Film Electroluminescent Devices: An Interference Effect," J. Phys. D: Appl. Phys., vol. 25, pp. 1010-1013 (1992).
Tuenge, R.T., "Current Status of Color TFEL Phosphors," Electroluminescence—Proceedings of the Sixth International Workshop on Electroluminescence, El Paso, Tex., pp. 173-177, May 1992.
Plasma Display Manufacturers of the American Display Consortium, "Recommended Research Topics on Plasma Display for the DARPA Sponsored Phosphor Center of Excellence," pp. 1-2, Mar. 24, 1993.
Yamamoto, Y., et al., "Optical Processes in Microcavities," Physics Today, pp. 66-73, Jun. 1993.
E.F. Schubert, E.F., et al., "Giant Enhancement of Luminescence Intensity in Er-doped Si/SiO$_2$ Resonant Cavities," Appl. Phys. Lett. vol. 61, No. 12, pp. 1381-1383, Sep. 21, 1992.
Yokoyama, H., "Physics and Device Applications of Optical Microcavities," Science, vol. 256, pp. 66-70, Apr. 3, 1992.
Haroche, S., et al., "Cavity Quantum Electrodynamics," Scientific American, pp. 54-62, Apr. 1993.
Depp, S.W., et al., "Flat Panel Displays," Scientific American, pp. 90-97, Mar. 1993.
Huo, D.T.C., et al., "Reticulated Single-Crystal Luminescent Screen," J. Electrochem. Soc., vol. 133, No. 7, pp. 1492-1497, Jul. 1986.
Hinds, E.A., "Spectroscopy of Atoms in a Micron-Sized Cavity," (date and periodical title unknown), pp. 18-19.
Whitaker, Jerry C., "Electronic Displays: Technology, Design, and Applications," McGraw-Hill, Inc., pp. 185-192 (1994).
Hecht, Jeff, "Diverse fiberoptic systems require varied sources," Laser Focus World, vol. 36, No. 1, pp. 155-161, Jan. 2000.
Hamberg, I. and Granqvist, C.G., "Evaporated Sn-doped In$_2$O$_3$ films: Basic optical properties and applications to energy-efficient windows," Journal of Applied Physics, vol. 60, No. 11, pp. R123-R159, Dec. 1, 1986.
World Watch, Photonics Spectra, "IR Reflective Coating Boosts Bulb's Output, Recycling of IR Energy Saves Power, Cuts Costs" pp. 40-41, Jan. 1991.
Jenmar Visual Systems, Sunnyvale, CA, 4 pages, no date, but at least as early as Oct. 15, 1998.
DDS™ Rear Projection Screens, LORS™ Reflection Screens, © 1998 Physical Optics Corporation, Torrance, CA, 2 pages.
Schott Glass Technologies, Inc., Schott Total Customer Care, Contrast Enhancement Filters, Duryea, PA, 6 pages, Jan. 1998.
Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.
Young, L., "Multilayer Interference Filters with Narrow Stop Bands," Applied Optics, vol. 6, No. 2, pp. 297-312, Feb. 1967.
Hemingway, D.J. and Lissberger, P.H., "Effective Refractive Indices of Metal-Dielectric Interference Filters," Applied Optics, vol. 6, No. 3, pp. 471-476, Mar. 1967.
Holloway, R.J. and Lissberger, P.H., "Theory of Induced-Transmission Filters in Terms of the Concept of Equivalent Layers," Journal of the Optical Society of America, vol. 62, No. 11, pp. 1258-1264, Nov. 1972.
Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.
Lissberger, P.H., "Coatings with Induced Transmission," Applied Optics, vol. 20, No. 1, pp. 95-103, Jan. 1, 1981.
Pelletier, E. and MacLeod, H.A., "Interference Filters with Multiple Peaks," Journal of the Optical Society of America, vol. 72, No. 6, pp. 683-687, Jun. 1982.
Da-Lite Screen Company, Inc., www.da-lite.com, 46 pages website downloads as of Oct. 8, 1998.
Stewart Filmscreen Corporation®, www.stewartfilm.com, 34 pages website downloads as of Oct. 8, 1998.
Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).
Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.
Deck, L., et al., "Two color light-emitting-diode source for high precision phase-shifting interferometry", Optics Letters, vol. 18, No. 22, Nov. 15, 1993, pp. 1899-1901.
Morgan, C. G., et al., "New Approaches to Lifetime-Resolved Luminescence Imaging", Journal of Fluorescence, vol. 7, No. 1, 1997, pp. 65-73.

* cited by examiner

| 5V | 0.2V | CH1<br>Duty Cycle: 42.1%<br>Frequency: 2.00 kHz | CH2<br>50.4%<br>2.00 kHz | 1.25MS/s | 0.1ms |

Vrms: 2.42V

Light Engine Power Stability (Cyan)

LIGHTING DESIGN OF HIGH QUALITY BIOMEDICAL DEVICES

CLAIM OF PRIORITY

This present application is a continuation application of U.S. patent application Ser. No. 13/416,125 filed Mar. 9, 2012, entitled "Lighting Design of High Quality Biomedical Devices" which is a continuation application of and claims priority to U.S. patent application Ser. No. 12/691,601, filed Jan. 21, 2010, entitled "Lighting Design of High Quality Biomedical Devices" which claims the benefit of priority under 35 U.S.C. §119(e) to U.S. Provisional Patent Application No. 61/147,040, filed on Jan. 23, 2009, entitled "Lighting Design of High Quality Biomedical Devices," all or which applications are incorporated herein by reference in their entirety.

FIELD OF THE INVENTION

The present invention relates to using Light Emitting Diodes for illumination.

BACKGROUND OF THE INVENTION

Among the trends redefining 21st century biomedical diagnostics and therapeutics is the design of low-cost portable analyzers. Because light is a powerful tool in many of today's most widely used life science instruments, high intensity, low cost light engines are essential to the design and proliferation of the newest bio-analytical instruments, medical devices and miniaturized analyzers. The development of new light technology represents a critical technical hurdle in the realization of point-of-care analysis.

SUMMARY OF THE INVENTION

Embodiments of the present invention are directed to methods and devices for converting the output of a specific color LED and generating a broader band of wavelengths of emission including not only the specific color but additional color output. Specific embodiments, as will be described below, minimize backward directed light while increasing the total range of wavelengths emitted.

Lighting for life sciences is a broad and general category. Not only are the source specifications varied but so too are the equally important optical delivery requirements. Spectral and spatial lighting requirements for sensing on the head of an optical probe or within a single cell in a flowing stream differ in output power by orders of magnitude from the requirements of a multi-analyte detection scheme on an analysis chip or within the wells of a micro-titer plate. The number of colors, spectral purity, spectral and power stability, durability and switching requirements are each unique. Illuminating hundreds of thousands of spots for quantitative fluorescence within a micro-array may be best served by projection optics while microscopes set demanding specifications for light delivery to overfill the back aperture of the microscope objective within optical trains specific to each scope body and objective design.

While lighting manufacturers cannot provide all things to all applications, it is precisely this breadth of demand for which a light engine can be designed. To that end, products are not simple sources, but rather light engines: sources and all the ancillary components required to provide pure, powerful, light to the sample or as close to it as mechanically possible. Such designs have resulted in products that embody a flexible, hybrid solution to meet the needs of the broad array of applications for biotech. A qualitative comparison of light engine performance as a function of source technology is summarized in Table 1.

TABLE I

A qualitative comparison of light engine performance as function of the source technology employed

| Source Technology | Useable Light | Uniformity | Temporal Response | Heat Generation | Durability | Cost |
|---|---|---|---|---|---|---|
| Arc Lamp | med | poor | none | high | low | high |
| Laser | high | poor | none | low | low | very high |
| LED | low | poor | fast | low | high | medium |
| Tungsten | low | poor | none | medium | low | medium |
| Light Pipe | high | high | fast | low | high | low |

Historically arc lamps are noted to be flexible sources in that they provide white light. The output is managed, with numerous optical elements, to select for the wavelengths of interest and for typical fluorescence based instruments, to discriminate against the emission bands. However their notorious instability and lack of durability in addition to their significant heat management requirements make them less than ideal for portable analyzers. Moreover, large power demands to drive them present a barrier to battery operation within a compact design.

Lasers require a trained user and significant safety precautions. While solid state red outputs are cost effective, the shorter wavelength outputs are typically costly, require significant maintenance and ancillary components. Color balance and drift for multi-line outputs is a serious complication to quantitative analyses based on lasers. Moreover, the bulk of fluorescence applications do not need coherent light, are complicated by speckle patterns and do not require such narrow-band outputs. Overcoming each of these traits requires light management and adds cost to the implementation of lasers for most bio-analytical tools.

Finally LEDs, have matured significantly within the last decades. LEDs are now available in a relatively wide range of wavelengths. However their output is significantly broad so as to require filtering. Additionally, output in the visible spectrum is profoundly reduced in the green, 500-600 not. The LED also presents trade-offs with respect to emission wavelength dependent intensity, broad emission spectrum (spectral half width on the order of 30 nm or more), poor spectral stability, and the wide angular range of emission. In addition, the process used to manufacture LED's cannot tightly control their spectral stability; anyone wishing to use LED's in applications requiring a good spectral stability must work directly with a supplier to essentially hand-pick the LED's for the particular application. Finally, LED's generate light over a wide angular range (50% of light intensity emitted at 70°). While optics can narrow the emission band and focus the light output, the resulting loss in power and increase in thermal output further limit the feasibility of LED light engines.

Most importantly, these light technologies cannot be readily improved for bioanalytical applications. The associated light engine market simply does not justify the large investment necessary to overcome fundamental performance limitations. As a result, analytical instrument performance and price is constrained by the light source with no clear solution in sight. Moreover the numerous manufacturers of lamps and lasers provide only a source, not an integrated light engine. Companies such as ILC Technology, Lumileds, Spectra-Physics, Sylvania and CoolLED require some sort of mechanics and or electro-optics such as acousto-optic tunable filters (AOTFs), excitation filters (with a wheel or cube holder), shutters and controllers.

While no one lighting solution can best satisfy all instrument architectures, a light pipe engine combines the best of solid state technologies to meet or outperform the traditional technologies listed in Table I on the basis of all figures of merit for all individual wavelengths. Key to this performance is the light pipe architecture. Single outputs, such as red from a diode laser, may be competitive. However, no family of outputs can by assembled that bests the light pipe disclosed herein. In an embodiment of the invention, a light pipe engine can emit narrowband light exceeding 500 mW/color with intensifies up to 10 W/cm$^2$ depending on the application. In an embodiment of the invention, bandwidths as narrow as 10 nm are achievable. While such output power and overall emission intensity is impressive, the most significant figure of merit for quantifying the value of any lighting subsystem for bio-analytics is the intensity of high quality illumination provided to the sample. This is a factor dictated by the instrument design and sample volume and clearly very application specific.

In the case of medical devices and portable diagnostics the present light pipe invention offers a smart alternative for light generation. The light pipe engine is an optical subsystem; it consists of lamp modules for each discrete output based on solid state technologies tailored to best satisfy that output requirement complete with collection and delivery optics. The capabilities of the light pipe engine are highlighted in Table 2. The high performance illumination provided by the light pipe engine is embodied in a single compact unit designed to replace the entire ensemble of lighting components. The sources, excitation filters, multicolor switching capabilities and fast pulsing are contained within one box such that no external optics or mechanics are required.

TABLE II

Light pipe engine metrics of an embodiment of the invention, designed to meet the needs for portable fluorescence assays and biomedical devices.

| Key Metrics: | |
| --- | --- |
| Spectral Output | Up to eight colors spanning UV-Vis-NIR<br>>_100 mW/spectral band<br>1-10 W/cm |
| Peak Wavelength | Optimal for different floors, adjustable bandwidths |
| Power Stability | >99% over 24 hours |
| Spectral Width | 10 to 50 nm |
| Spectral Drift | <1% in 24 hours |
| Color Dependence | None |
| Lifetime | >5000 hrs |
| Footprint | amenable to portability |
| Maintenance | None, no replacement components for the light engines lifetime |

An inexpensive lighting solution, uniquely well suited to the production of safe, effective and commercially viable life science tools and biomedical devices can be attained using a solid-state light engine. In an embodiment of the invention, this light engine can provide powerful, pure, stable, inexpensive light across the Ultraviolet-visible-near infrared (UV-Vis-NIR). Light engines are designed to directly replace the entire configuration of light management components with a single, simple unit. Power, spectral breadth and purity, stability and reliability data will demonstrate the advantages of these light engines for today's bioanalytical needs. Performance and cost analyses can be compared to traditional optical subsystems based on lamps, lasers and LEDs with respect to their suitability as sources for biomedical applications, implementation for development/evaluation of novel measurement tools and overall superior reliability. Using such sources the demand for portable, hand-held analyzers and disposable devices with highly integrated light sources can be fulfilled.

Lamp

In various embodiments of the present invention, a lamp emits wavelengths of light, which excite fluorescence from photosensitive targets in the sample of interest. In various embodiments of the present invention, a lamp can be in the form of a tube, rod, or fiber of varying or constant diameter. In various embodiments of the present invention, a constituent light pipe can be made of glass, plastic, single or multiple inorganic crystal(s), or a confined liquid. In various embodiments of the present invention, a pipe either contains or is coated with a layer or layers containing, a narrowband luminescent material such as organic or inorganic compounds involving rare earths, transition metals or donor-acceptor pairs. In various embodiments of the present invention, a lamp emits confined luminescence when excited by IR, UV, or visible light from an LED, Laser, fluorescent tube, arc lamp, incandescent lamp or other light source. In an embodiment of the present invention, a lamp operates through the process of spontaneous emission, which results in a much larger selection of available wavelengths than is available for efficient stimulated emission (laser action).

Relay Optics

In an embodiment of the present invention, relay optics consist of light pipes, optical fibers, lenses and filters, which optically transport the light from a lamp to one or more capillaries and light pipes, optical fibers, lenses and filters which collect and transport any generated fluorescence to an appropriate detector or array of detectors, in conjunction with adaptors for coupling the excitation light into the capillaries, coupling the emission light out of the capillaries and for enhancing physical discrimination of the excitation and emission. In an embodiment of the present invention, relay optics, including fibers, can be constructed in a loop or as a cavity so that light from a lamp can pass through one or more capillaries multiple times to enhance excitation efficiency.

In an embodiment of the present invention, a number of lamps each emitting one or more color of light can have their constituent light pipes coupled in parallel or in series acting to produce multiple colors simultaneously or in sequence. In an embodiment of the present invention, one or more lamps can illuminate single channels, multiple parallel channels, multiple channels in multiple dimensions, numerous spots along the analysis channel and/or reservoirs connected to the flow streams.

In an embodiment of the present invention, lamps can be illuminated continuously during the measurement process or can be pulsed on and off rapidly to enable time-based detection methods. In an embodiment of the present invention, a lamp can be switched off between measurements, to eliminate the heat output. This can be contrasted with alternatives such as arc lamps or lasers that are unstable unless they are operated continuously.

Illumination and Collection System

In an embodiment of the present invention, a flexible illumination and collection system for capillary/fluorescence apparatus allows for a varying number of samples to be analyzed simultaneously. 'Simultaneously' is herein defined as occurring close in time. Two light pipes can irradiate two capillaries at the same time and the fluorescence from the molecules in one of the capillaries can be delayed due to physical or chemical effects relating to absorption, phosphorescence and/or fluorescence resulting in a delay in the fluorescence from the molecules in one of the capillaries. This excitation is still considered to result in 'simultaneous detection'. In an embodiment of the present invention, an illumination and collection system can be adjusted for uniform illumination of multiple capillaries. In an embodiment of the present invention, illumination systems can irradiate an array of channels in an array of capillaries. In an embodiment of the present invention, an array of channels can be etched, molded, embossed into the capillaries. In an embodiment of the present invention, a set of wells intimately connected to fluidic conduits can be stepped along the length of the fluidic conduit such that they can be interrogated at numerous sites for the purposes of creating a map or image of the reacting species.

In an embodiment of the present invention, an illumination and collection system can emit multiple colors as desired. In an embodiment of the present invention, an illumination and collection system can be pulsed on and off as desired to reduce heat generation. In an embodiment of the present invention, an illumination and collection system can be pulsed on and off to allow time-based fluorescence detection.

In an embodiment of the present invention, illumination systems can irradiate homogeneous reactions within fluidic conduits or reservoirs. In an embodiment of the present invention, illumination systems can irradiate heterogeneous reactions on the surface of fluidic conduits or reservoirs. In an embodiment of the present invention, illumination systems can irradiate homogeneous or heterogeneous reactions on the surface of or within the pores of a porous reaction support.

Other objects and advantages of the present invention will become apparent to those skilled in the art from the following description of the various embodiments, when read in light of the accompanying drawings.

BRIEF DESCRIPTION OF THE FIGURES

Various embodiments of the present invention can be described in detail based on the following figures, wherein.

DETAILED DESCRIPTION OF THE INVENTION

Figure 1:
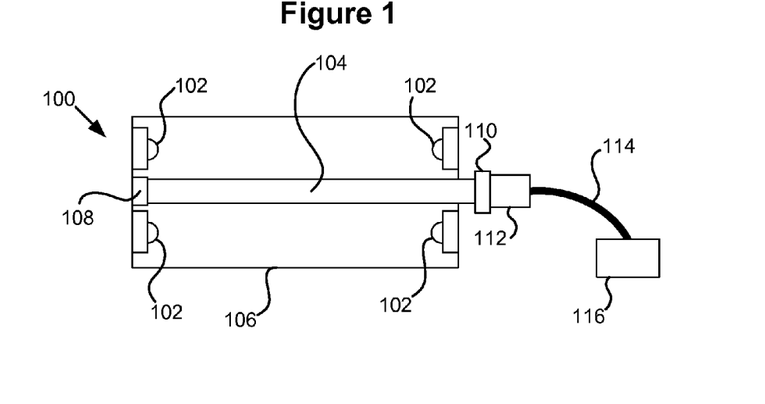
FIG. 1 shows a schematic of a light engine subsystem consisting of a lamp module and delivery optics.

Shown in FIG. 1, is the light pipe engine 100 of an embodiment of the invention. An individual lamp module driven by light pipe technology consists of an excitation source 102, typically one or more LEDs, and a light pipe 104. In an embodiment, the excitation source 102 and light pipe 104 can be housed in a cylindrical waveguide 106. The excitation source 102 drives luminescence in the light pipe 104, which is composed of a glass or polymer fiber. In an embodiment, light pipe 104 includes a mirror 108. Glass fibers are either doped with a rare earth metal or activated with a transition metal. Polymer fibers are doped with a dye. The fibers have fast response and decay times and can achieve a high efficiency through the design of delivery optics. The design and selection of the fiber determines the peak wavelength of the output illumination; options exist to span the UV-Vis-NIR spectrum. The bandwidth of the luminescence is narrow and can be further defined with the use of band pass filters 110 integrated into the delivery optics. In an embodiment, the delivery optics may include a band pass filter 110 connected to a coupler 112, which can be attached to an optical delivery pipe 114 which leads to an instrument (e.g., a microtiter plate) 116. Output intensity is determined through the design of the pipe's excitation source.

The light pipe geometry provides a unique opportunity to shape and direct the angular and spatial range of outputs. Combined with a high output power, the delivery optics can be readily tailored to couple the light with various instruments and analyzers. Sensors, optical probes, microscope objectives or through liquid light guides, two-dimensional oligomer and micro fluidic chips, and micro titer plates are all illumination fields that light pipe engines can readily support. Moreover, high output power enables illumination of large areas within a chip, micro array or micro titer plate and, as a result, support high-speed throughput in instruments where to date only scanning modes of operation could be envisioned.

The preferred mode of light pipe excitation is the application of one or more LED's. This approach takes advantages of the benefits of LED illumination: low cost, durability, and, at an appropriate excitation wavelength, high output power to drive the light pipe. In so doing the LED's shortcomings are managed. The lack of spectral stability and the high angular output characteristic of LED's do not impact the luminescence of the light pipe. Instead, the innovation of the light pipe enables circumvention of the principle of etendue conservation. All light sources must conform to this dictate, which requires the spread of light from a source never exceed the product of the area and the solid angle. Etendue cannot decrease in any given optical system.

The ability to modulate solid-state source outputs provides a unique opportunity for multiplexed fluorescent assays. Current light engine designs employ solid state materials with fast luminescence (approximately 10 ns.) The light pipe and LED have similar modulation capabilities thus multiple light pipes tuned to different output wavelengths can be employed to selectively detect multiple fluorescent tags within a given analysis. In addition, pulse modulation and phase modulation techniques enable fluorescence lifetime detection and afford improved signal to noise ratios. Each of the solid state units is truly off when it is off so low background signals and high contrast ratios are possible.

Table III shows an embodiment of the present light pipe engine invention's product and performance features. As improvements are made to LED's and the cost of semiconductor lasers continue to decline, the tool chest of options available to light lipe engines will continue to evolve. The desired light engine can ultimately be powered by a combination of light pipe, LED's and lasers. The knowledge and competency to integrate any of these lighting technologies into the delivery optics supports the requirements of each specific application and provides technical and commercial value.

TABLE III

The light pipe engine feature set.

| | |
|---|---|
| Wavelengths | UV-Vis-NIR |
| Colors | Up to eight |
| Intensity | 1-10 W/cm$^2$ |
| Bandwidths | Adjustable |
| Size | Compact |
| Ease of Use | Yes |
| Modulation | Up to 5 kHz |
| Color control | Independent |
| System Control | Manual or computer |
| Heat output | Minimal |
| Life time | Long |

Eight Light Engine Subsystem

Figure 5:
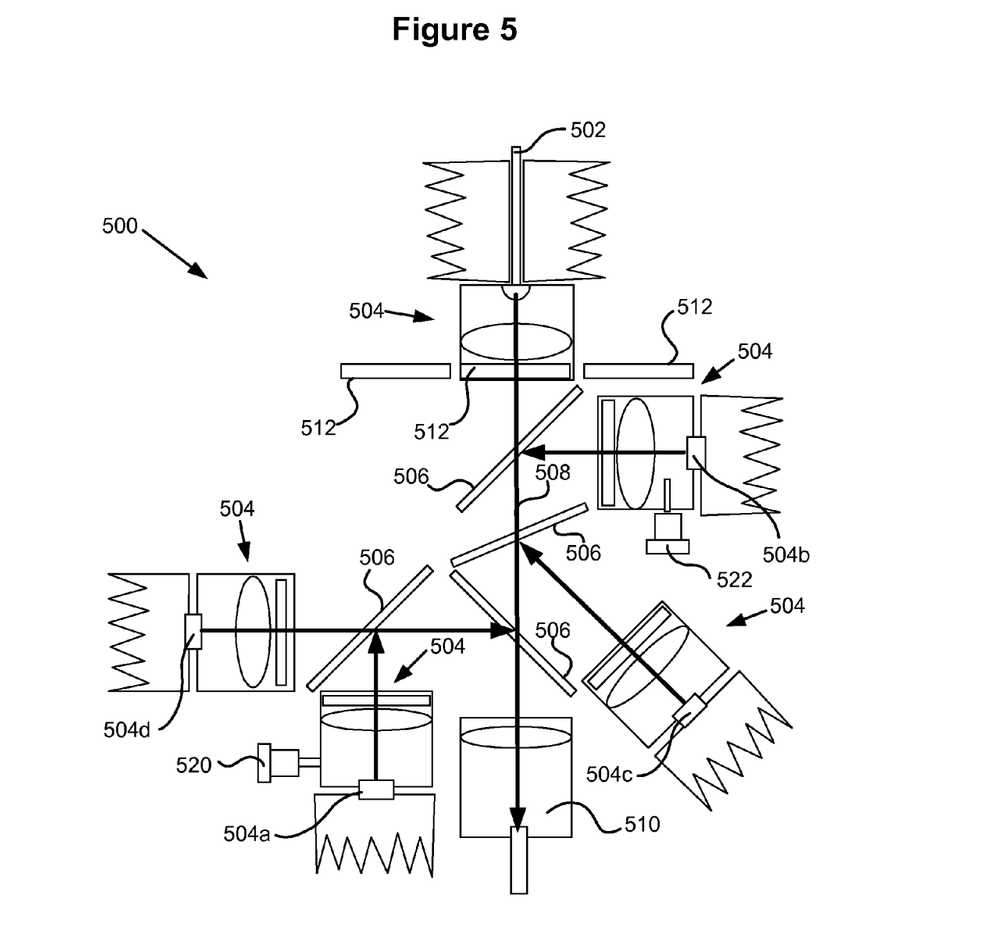
FIG. 5 shows an eight color light engine layout, including a light pipe and five other solid state light sources, with dichroic mirrors to create a single coaxial 8-color beam. Each individual light source is collimated so as to be efficiently combined and after color combination, the beam is refocused into a light guide for transport to the device or system to be illuminated according to an embodiment of the invention.

FIG. 5 shows a schematic for a eight color light engine layout. In an embodiment of the invention, a eight color light engine 500 includes a luminescent rod 502 and five other solid state light sources 504, with dichroic mirrors 506 to create a single coaxial 8-color beam 508 (for example selected from UV 395, Blue 440, Cyan 485, Teal 515, Green 550 or 575, Orange 630 and Red 650 nm) leading to an output 510. In this embodiment, a manual or electromechanical filter slider 512 allows green yellow filtering of YAG generating 550 or 575 nm light. Additional colors can be used. For example, a color band centered at 550 nm can be replaced with a color band centered at 560 nm. Each individual light source is collimated so as to be efficiently combined and after color combination, the beam is refocused into a light guide for transport to the device or system to be illuminated according to an embodiment of the invention.

The light engine subsystem is designed to interface to the array of bioanalytical tools with the expectation that the end user can take for granted the high quality of the illumination. Table IV summarizes four bioanalytical applications for which light engines including light pipes could replace more traditional illumination subsystems and offer performance and cost advantages. For example, Kohler illumination in transmitted light microscopy requires that the light be focused and collimated down the entire optical path of the microscope to provide optimal specimen illumination. Even light intensity across a fairly large plane is a critical requirement. For stereomicroscopy, lighting is achieved with ring-lights at the objective and fiber optic lights pointed at the specimen from the side. In both cases, the light engine must efficiently couple to a fiber optic cable.

For portable diagnostic tools, the delivery optics must provide even illumination over a small volume. These requirements are similar to, but less restrictive than those presented by capillary electrophoresis. Capillary electrophoresis requires an intense (10 mW) light focused onto the side of a capillary tube with characteristic dimensions on the order of a 350 pm outer diameter and a 50 pro inner diameter. To achieve this goal, the delivery optics were comprised of a ball lens to collect and collimate light from the lamp module (already coupled into an optical fiber), a bandpass filter to provide a narrowbandwidth of illumination, and an aspheric lens to focus the light at the center of the capillary bore. This approach yielded an 80 pin spot size and the desired 10 mW of delivered power to the capillary tube.

The design of delivery optics for microfluidic immunoassays requires both the even illumination required for optical microscopy and the small volume illumination required for capillary electrophoresis. Light engines capable of delivering even illumination at the active sites in a microfluidic array for detection of fluorescent tagged biomarkers have been designed for immunochemical as well as genomic applications. The advantages of the luminescent light pipe are providing commercial, readily available light engine solutions for illumination-detection platforms optimized for portable diagnostic tools.

Spectral Bands and Output Power

Figure 2:
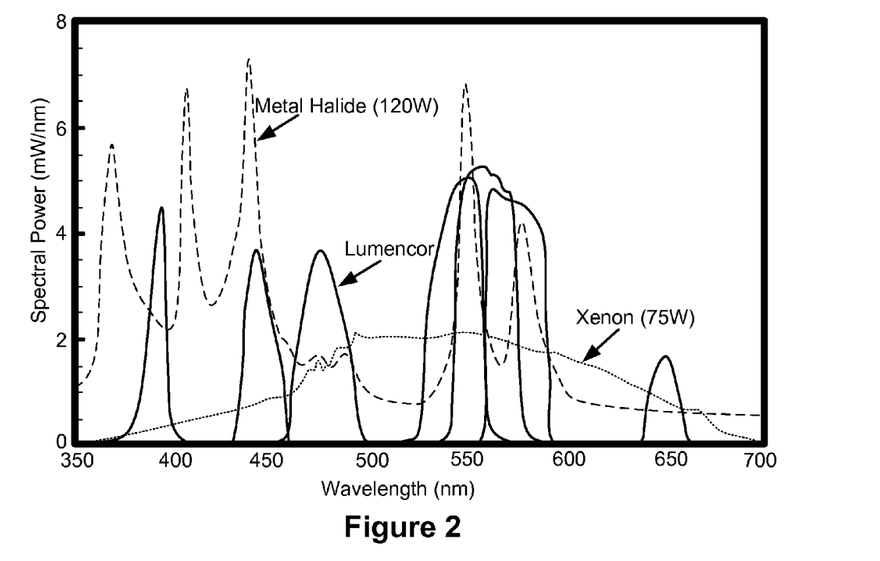
FIG. 2 shows light engine output relative to a typical metal halide lamp and 75 W xenon bulb.

In various embodiments of the present invention, the light pipe engine performs well compared with the output power across the visible spectrum to other lamps (see FIG. 2). Such comparisons beg for disclaimers as the outputs of the commonly employed lamps change in time and degrade with usage. The light pipe engine is all solid state so they it is significantly more stable and reproducible. FIG. 2 was taken within the manufacturers' specified lifetime for each lamp, by an independent user well trained in biophotonics, these outputs represent typical performances of a common metal halide bulb, 75 W xenon bulb and that of the light pipe engine.

Such output comparisons are further complicated by mismatches between the spikes of the metal halide bulb and light pipe light engine output bands, However, noting such disparities it is fair to claim the outputs of the light engine across the visible spectrum compare well against the outputs of a metal halide bulb in spectral windows that match the excitation energies of some of the most commonly used fluors for biotech: around 390 nm where DAPI and Hoescht can be excited;

TABLE IV

Performance and cost analysis of the light pipe engine vs. traditional illumination subsystems in four key bioanalytical applications

| specification | Sanger Sequencing | | Q-PCR | | Flow Cytometry | | Fluorescence Microscopy | |
|---|---|---|---|---|---|---|---|---|
| Light engine | Light Pipe | Ar Ion Laser | Light Pipe | Metal Halide | Light Pipe | Lasers | Light Pipe | Metal Halide |
| Intensity W/cm$^2$ | 150-250 | 150-250 | 0.5-1 | 0.2-1, very λ specific | 150-250 | 150-250 | <50 | 1-50, very λ specific |
| Wavelength | 505 nm | multiline | 4 colors | | >2 colors | | 4 colors | |
| Bandwidth, nm | 10-30 | 26 | 10-30 | 15 | 10-30 | <5 | 10-30 | 15 |
| Stability | 0.1% | >1% | 0.1% | >1% | 0.1% | >1% | 0.1% | >1% |
| Switching, ms | <0.03 | 1-10, ext. shutter | <0.03 | 40, ext. shutter | <0.03 | 1-10, ext. shutter | <0.03 | 40, ext. shutter |
| MTBF, hrs | >10,000 | <4,000 | >10,000 | <1,000 | >10,000 | <4,000 | >10,000 | <1,500 |
| Price | <$3K | >$5K | <$7.5K | >$10K | <$5K | >$5K | <$7.5K | >$10K | in the window most commonly associated with a cyan line of an argon ion laser and often used to excite Alexa dyes, green fluorescent proteins and fluoresceins; and in the red where neither of the lamps provides appreciable power for the likes of Cy5. The light engine also bests the Xenon lamp across the palate of excitation wavelengths most common to biotech: the Xenon lamp underperforms particularly in the violet, cyan, blue and red regions of the visible spectrum. Of course, more powerful Xenon lamps are often employed to provide enhanced performance at a significant maintanence cost.

In another embodiment of the present invention, as seen in FIG. 2, the output of the green and amber bands have essentially doubled, such that on a photon per photon basis the area under the curve for the arc lamp vs. light engine are the same. Certainly the peak shapes, and figures of merit (height, FWHM, etc.) differ. However, no compromise in output power, even for the 546 nm band of the arc lamp, should be incurred as a consequence of using a light pipe engine replacement.

Alternatively, a light pipe engine can be employed in a short duty cycle mode for power starved applications. When feasible, pulse widths of less than 100 ms at 10% duty cycles can actually improve the power output per band by a factor of 1.5 to 2.0 over longer duty cycles or in continuous mode of operation. Applications that employ multiple lasers and acousto-optic tunable filters (AOTFs) but need safe, cost effective and easy to employ lighting solutions might benefit from such light engine performance. Fluorescence microscopy for multicolor detection could take advantage of this option, for example. As could numerous other bioanalytical platforms such as a light engine replacement for the optical excitation from AOTF-based multicolor fluorescence detection for short tandem repeat (STR) analysis in a micro-eletrophoretic device, a glass microchip.

Fast Switching

Figure 3:
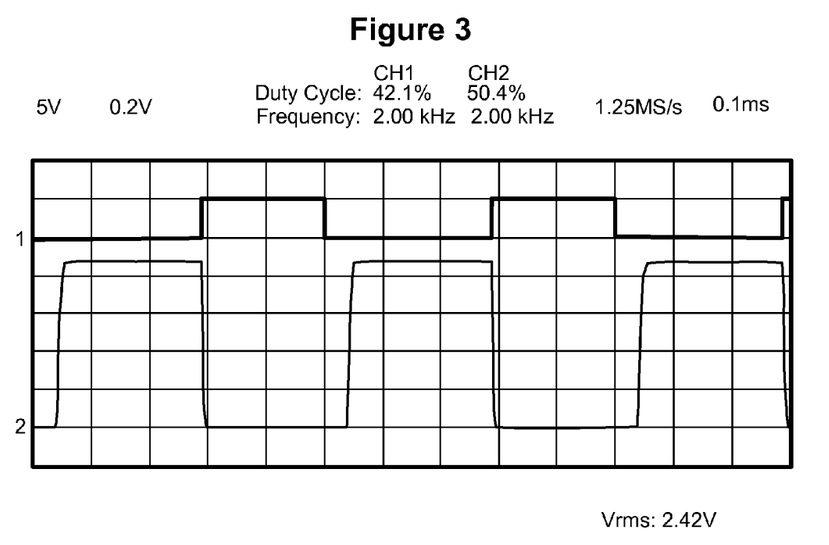
FIG. 3 shows light pipe engine with <10 ns rise and fall times for fast switching between bands.

Because of the solid state nature and independently operable designs of the lamp modules, coupled to fast (approximately 10 ns) decay times of typical materials employed, a light pipe based light engine outperforms any broad spectrum source in terms of support for fast analyses. Lamp based sources are coupled to filters and/or shutters with mechanical supports that relegate them 1 to 50 millisecond regimes. Even LED based lamps require filtering for most quantitative fluorescence based analyses. The light pipe based light engine incorporates all that filtering into its highly integrated design. Therefore switching times are limited today by the electronics of the boards controlling the sources. Rise times of less than 20 μs and fall times of less than 2 us are typical (see FIG. 3). Moreover each color can be switched independently and is compatible with triggering by TTL, RS232 and USB and intensity control by RS232, USB or manually. This supports experiments where simultaneous excitation of multiple tags could previously only be done with multipass excitation filters and broadband sources. Using a light pipe engine, effectively instantaneous excitation of individual reporters can be manipulated within microsecond time frames to achieve rapid, serial exposure of a biologic event to the various excitation bands with no external hardware beyond the light engine itself.

Stability

Figure 4:
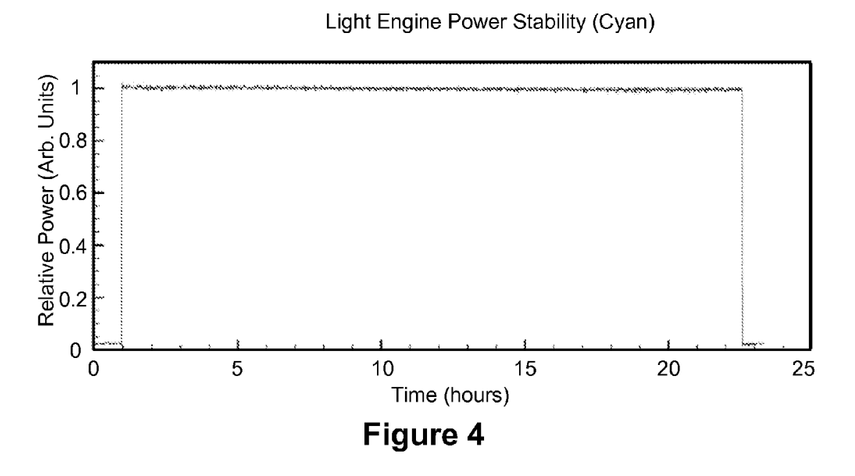
FIG. 4 shows light engine stability over 24 hours of use.

Because a light pipe based light engine is based on solid state technologies, they are extremely stable both in short duration experiments and over long term use. FIG. 4 depicts this stability. Light engines are powered by 24 V power supplies operated in DC mode, therefore there is no 60 Hz noise. All colors perform similarly. In 24 hours of continuous operation, the output fluctuates on the order of 1%. Short term stability on the order of 1.0 ms is approximately 0.5%. Short term stability for 0.1 ms is diminished by a factor of ten to 0.05%.

The foregoing description of the various embodiments of the present invention has been provided for the purposes of illustration and description. It is not intended to be exhaustive or to limit the invention to the precise forms disclosed. Many modifications and variations will be apparent to the practitioner skilled in the art. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

Other features, aspects and objects of the invention can be obtained from a review of the figures and the claims. It is to be understood that other embodiments of the invention can be developed and fall within the spirit and scope of the invention and claims

What is claimed is:

1. A solid-state light engine comprising:
   a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;
   a first LED light module, wherein the first LED light module includes at least a first LED adapted to emit first light of a first color different than the luminescent color;
   a second LED light module, wherein the second LED light module includes at least a second LED adapted to emit second light of a second color different than the first color and the luminescent color;
   a third LED light module wherein the third LED light module includes at least a third LED adapted to emit third light of a third color different than the first color, the second color, and the luminescent color;
   a plurality of dichroic elements adapted to direct each of the luminescent light, the first light, the second light and the third light into an output light beam; and
   an optical output element adapted to couple the output light beam to an optical instrument wherein the solid state light engine is capable of emitting narrowband light exceeding 500 mW per color with intensities up to 10 W/cm$^2$.

2. A solid-state light engine comprising:
   a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;
   a first LED light module, wherein the first LED light module includes at least a first LED adapted to emit first light of a first color different than the luminescent color;
   a second LED light module, wherein the second LED light module includes at least a second LED adapted to emit second light of a second color different than the first color and the luminescent color;
   a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein the solid state light engine can be pulsed on and off rapidly to enable time-based detection methods.

3. A solid-state light engine comprising:

a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein the solid state light engine can be pulsed on and off at a frequency greater than 2 kHz.

4. A solid-state light engine comprising:

a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein the solid state light engine can be pulsed on and off at a frequency of about 5 kHz.

5. The solid state light engine of claim 1, in combination with an optical instrument coupled to the optical output element, wherein the optical instrument is selected from the group consisting of: a sensor; an optical probe; a microscope; a liquid light guide; a fiber optic cable; a micro fluidic chip; and a micro titer plate.

6. The solid state light engine of claim 1, wherein each color can be switched independently.

7. A solid-state light engine comprising:

a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein each color can be switched independently in 30 µs or less.

8. A solid-state light engine comprising:

a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein the luminescent color is green, the first color is red, the second color is blue, and the third color is cyan.

9. A solid-state light engine comprising:

a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and a fourth LED light module wherein the fourth LED light module includes at least a fourth LED adapted to emit fourth light of a fourth color different than the first color, the second color, the third color, and the luminescent color; and wherein the plurality of dichroic elements is adapted to direct each of the luminescent light, the first light, the second light, the third light, and the fourth light toward the optical output element for transmission to said optical instrument.

10. The solid state light engine of claim 1, wherein the luminescent material includes one or more of rare earths, transition metals, and donor-acceptor pairs.

11. The solid state light engine of claim 1, further comprising at least one laser diode for emitting laser light.

12. The solid state light engine of claim 1, wherein output color is compatible with triggering by one or more of TTL, RS232, and USB.

13. A solid-state light engine comprising:
a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein the solid state light engine is adapted for simultaneous excitation of multiple fluorescent tags.

14. A solid-state light engine comprising:
a lamp which includes a rod and a solid state light source, wherein in the rod includes a narrowband luminescent material, and wherein the solid state light source is adapted to emit light to excite the narrowband luminescent material such that the narrowband luminescent material emits luminescent light of a luminescent color by spontaneous emission;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a third LED light module wherein the third LED light module includes at least a third LED adapted to emit third light of a third color different than the first color, the second color, and the luminescent color;

a plurality of dichroic elements adapted to direct each of the luminescent light, the first light, the second light and the third light into an output light beam; and an optical output element adapted to couple the output light beam to an optical instrument; and wherein the solid state light engine is adapted for rapid serial excitation of multiple different fluorescent tags in microsecond timeframes.

15. A solid-state light engine comprising:
a lamp which includes a rod and an LED light source, wherein in the rod includes a luminescent material, and wherein the LED light source is adapted to emit light to excite the luminescent material such that the luminescent material emits luminescent light of a luminescent color;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a plurality of dichroic elements adapted to direct each of the luminescent light, the first light, and the second light into an output light beam;

an optical output element adapted to couple the output light beam to a microscope; and wherein the solid state light engine is capable of emitting narrowband light exceeding 500 mW per color.

16. A solid-state light engine comprising:
a lamp which includes a rod and an LED light source, wherein in the rod includes a luminescent material, and wherein the LED light source is adapted to emit light to excite the luminescent material such that the luminescent material emits luminescent light of a luminescent color;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a plurality of dichroic elements adapted to direct each of the luminescent light, the first light, and the second light into an output light beam;

an optical output element adapted to couple the output light beam to a microscope; and wherein the solid state light engine can be pulsed on and off at a frequency greater than 2 kHz.

17. A solid-state light engine comprising:
a lamp which includes a rod and an LED light source, wherein in the rod includes a luminescent material, and wherein the LED light source is adapted to emit light to excite the luminescent material such that the luminescent material emits luminescent light of a luminescent color;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a plurality of dichroic elements adapted to direct each of the luminescent light, the first light, and the second light into an output light beam;

an optical output element adapted to couple the output light beam to a microscope; and wherein each color can be switched independently in 30 µs or less.

18. The solid state light engine of claim 15, wherein the luminescent color is green, the first color is red, and the second color is blue.

19. The solid state light engine of claim 15, further comprising:

a third LED light module wherein the third LED light module includes at least a third LED adapted to emit third light of a third color different than the first color, the second color, and the luminescent color; and wherein the plurality of dichroic elements is adapted to direct each of the luminescent light, the first light, the second light, and the third light toward the optical output element for transmission to said optical instrument.

20. The solid state light engine of claim 15, wherein output color is compatible with triggering by one or more of TTL, RS232, and USB.

21. A solid-state light engine comprising:

a lamp which includes a rod and an LED light source, wherein in the rod includes a luminescent material, and wherein the LED light source is adapted to emit light to excite the luminescent material such that the luminescent material emits luminescent light of a luminescent color;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a plurality of dichroic elements adapted to direct each of the luminescent light, the first light, and the second light into an output light beam;

an optical output element adapted to couple the output light beam to a microscope; and wherein the solid state light engine can be adapted for simultaneous excitation of multiple fluorescent tags.

22. A solid-state light engine comprising:

a lamp which includes a rod and an LED light source, wherein in the rod includes a luminescent material, and wherein the LED light source is adapted to emit light to excite the luminescent material such that the luminescent material emits luminescent light of a luminescent color;

a first LED light module, wherein the first LED light module includes at least a first LED adapted to emit first light of a first color different than the luminescent color;

a second LED light module, wherein the second LED light module includes at least a second LED adapted to emit second light of a second color different than the first color and the luminescent color;

a plurality of dichroic elements adapted to direct each of the luminescent light, the first light, and the second light into an output light beam;

an optical output element adapted to couple the output light beam to a microscope; and wherein the solid state light engine can be adapted for rapid serial excitation of multiple different fluorescent tags in microsecond timeframes.

23. A solid-state light engine comprising:

a lamp which includes a luminescent rod and a solid state light source, wherein in the luminescent rod includes a luminescent material, and wherein the solid state light source is adapted to emit light to excite the luminescent material such that the luminescent material emits green light;

a first LED light module, wherein the first LED light module includes at least a first LED adapted to emit red light;

a second LED light module, wherein the second LED light module includes at least a second LED adapted to emit blue light;

a plurality of dichroic elements adapted to direct each of the luminescent light, the first light, and the second light into an output light beam;

an optical output element adapted to couple the output light beam to a microscope.

24. The solid state light engine of claim 23, wherein the solid state light engine can be pulsed on and off at a frequency greater than 2 kHz.

25. The solid state light engine of claim 23, wherein each color can be switched independently in 30 µs or less.

26. The solid state light engine of claim 23, wherein output color is compatible with triggering by one or more of TTL, RS232, and USB.

27. The solid state light engine of claim 23, wherein the solid state light source is an LED light source.

28. The solid state light engine of claim 23, further comprises one or more additional led light sources which produce one or more additional colors of light selected from UV, Cyan, Teal and Orange.

* * * * *

UNITED STATES PATENT AND TRADEMARK OFFICE
CERTIFICATE OF CORRECTION

PATENT NO. : 8,309,940 B2  
APPLICATION NO. : 13/484031  
DATED : November 13, 2012  
INVENTOR(S) : Claudia B. Jaffe et al.

Page 1 of 1

It is certified that error appears in the above-identified patent and that said Letters Patent is hereby corrected as shown below:

In the Specification

Col. 7, line 22, after "510." insert

-- Output 510 couples beam 508 from light engine 500 to a liquid light guide (LLG), optical fiber, kohler etc. --

Col. 7, line 31, after "invention." insert

-- In embodiments, solid state light sources 504 include: blue LEDs and UV LEDs combined in module 504a; red and orange LEDs combined in module 504b; teal LEDs in module 504c, and cyan LEDs in module 504d. In embodiments luminescent rod 502 generates green light. In an optional embodiment, a laser diode 520 emitting 375nm or 395nm laser light is coupled to module 504a. In an optional embodiment, laser diodes 522 emitting 630nm and 650nm laser light are coupled to module 504b. --

Signed and Sealed this  
Twenty-fifth Day of February, 2014

Michelle K. Lee  
*Deputy Director of the United States Patent and Trademark Office*